(12) United States Patent
Pappe et al.

(10) Patent No.: US 11,045,113 B2
(45) Date of Patent: Jun. 29, 2021

(54) METHOD FOR DETERMINING THE ALIGNMENT OF A SYSTEM, AND A DISPLAY SYSTEM

(71) Applicant: OTTO BOCK HEALTHCARE GMBH, Duderstadt (DE)

(72) Inventors: Alexander Pappe, Vienna (AT); Alexander Glier, Gottingen (DE); Mark Schonemeier, Gottingen (DE); Martin Pusch, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 223 days.

(21) Appl. No.: 15/310,063

(22) PCT Filed: May 8, 2015

(86) PCT No.: PCT/DE2015/100186
§ 371 (c)(1),
(2) Date: Nov. 9, 2016

(87) PCT Pub. No.: WO2015/169288
PCT Pub. Date: Nov. 12, 2015

(65) Prior Publication Data
US 2017/0135608 A1  May 18, 2017

(30) Foreign Application Priority Data
May 9, 2014 (DE) .......................... 102014006690.8

(51) Int. Cl.
*A61B 5/107* (2006.01)
*A61B 5/103* (2006.01)
*A61B 5/00* (2006.01)

(52) U.S. Cl.
CPC .......... *A61B 5/1079* (2013.01); *A61B 5/1036* (2013.01); *A61B 5/1072* (2013.01); *A61B 5/4851* (2013.01); *A61B 5/743* (2013.01)

(58) Field of Classification Search
CPC ..... A61B 5/1079; A61B 5/4851; A61B 5/743; A61B 5/1072; A61B 5/103; A61B 5/1036–1038; A61B 5/112
See application file for complete search history.

(56) References Cited

U.S. PATENT DOCUMENTS 3,894,437 A * 7/1975 Hagy .................. A61B 5/1036
600/592
4,267,728 A * 5/1981 Manley ................ A43B 3/0005
345/629

(Continued)

FOREIGN PATENT DOCUMENTS

DE 4418475 A1 11/1995
DE 102004047325 A1 4/2005
(Continued)

OTHER PUBLICATIONS

PCT International Search Report for PCT International Patent Application No. PCT/DE2015/100186, dated Sep. 11, 2015.

*Primary Examiner* — Thaddeus B Cox
(74) *Attorney, Agent, or Firm* — Holland & Hart, LLP (57) ABSTRACT

A method for determining the alignment of a system, wherein the system includes measuring and display devices. The measuring device has a measuring platform and detects horizontal and vertical forces that are exerted by a person located on the measuring platform. The system also includes at least one camera device used to at least partially photograph the person located on the measuring platform. The method includes transmitting image data from the at least one camera device and measurement data from the measuring device to the display device, superimposing a force (Continued)

application line in the display device on the image data, and displaying the force application line on the image of the person located on the measuring platform. The method also includes detecting marker points with a fixed geometric relation to the measuring platform by the at least one camera device, wherein the geometric relationship of the marker points to one another is known, and determining the position and/or orientation of the measuring platform to the at least one camera device via an image evaluation of the detected marker points.

16 Claims, 5 Drawing Sheets

(56) References Cited

U.S. PATENT DOCUMENTS

| | | | | |
|---|---|---|---|---|
| 4,416,293 | A | * | 11/1983 | Anderson ............ A63B 22/02 348/77 |
| 4,598,717 | A | * | 7/1986 | Pedotti ............... A61B 5/1036 600/592 |
| 4,600,016 | A | * | 7/1986 | Boyd .................. A61B 5/1038 600/592 |
| 4,631,676 | A | * | 12/1986 | Pugh .................. A61B 5/1038 348/77 |
| 4,906,193 | A | * | 3/1990 | McMullen ............ G09B 19/00 273/DIG. 27 |
| 5,080,109 | A | * | 1/1992 | Arme, Jr. .............. A61B 5/103 33/515 |
| 5,269,318 | A | * | 12/1993 | Nashner ............. A61B 5/0488 600/595 |
| 5,623,944 | A | * | 4/1997 | Nashner ............. A61B 5/1036 600/592 |
| 5,885,229 | A | * | 3/1999 | Yamato .............. A61B 5/1038 600/587 |
| 6,231,527 | B1 | * | 5/2001 | Sol ..................... A61B 5/1038 348/143 |
| 6,423,015 | B1 | * | 7/2002 | Winkenbach ........ A61B 5/1079 600/587 |
| 8,679,036 | B2 | | 3/2014 | Pusch et al. |
| 8,845,556 | B1 | * | 9/2014 | Schickler ............ A61B 5/1036 340/573.7 |
| 2002/0099509 | A1 | * | 7/2002 | Peisner ................ G01L 5/161 702/41 |
| 2005/0069195 | A1 | | 3/2005 | Uezono et al. |
| 2005/0171456 | A1 | * | 8/2005 | Hirschman ......... A61B 5/1036 600/592 |
| 2005/0182341 | A1 | * | 8/2005 | Katayama ............. A61B 5/103 600/587 |
| 2007/0275830 | A1 | | 11/2007 | Lee et al. |
| 2009/0118647 | A1 | * | 5/2009 | Pusch ................. A61B 5/1036 600/587 |
| 2009/0240171 | A1 | * | 9/2009 | Morris Bamberg ........ A61B 5/1038 600/595 |
| 2009/0247909 | A1 | * | 10/2009 | Mukumoto ............. A43B 7/28 600/592 |
| 2010/0094174 | A1 | | 4/2010 | Choi et al. |
| 2010/0246898 | A1 | * | 9/2010 | Izumi ..................... A63B 6/00 382/106 |
| 2011/0025853 | A1 | * | 2/2011 | Richardson .......... H04N 5/2256 348/159 |
| 2011/0260890 | A1 | * | 10/2011 | Larsen ............... A63B 69/3667 341/20 |
| 2012/0086659 | A1 | * | 4/2012 | Perlin .................... G06F 3/005 345/173 |
| 2012/0094814 | A1 | * | 4/2012 | Atkins ................. A61B 5/486 482/142 |
| 2012/0130280 | A1 | * | 5/2012 | Lee ..................... A61B 5/0004 600/587 |
| 2012/0165162 | A1 | * | 6/2012 | Lu ..................... A63B 22/0235 482/54 |
| 2012/0271565 | A1 | | 10/2012 | Berme et al. |
| 2013/0029791 | A1 | * | 1/2013 | Rose ................. G09B 19/0038 473/409 |
| 2013/0053702 | A1 | * | 2/2013 | Pfeiffer ............... A61B 5/0064 600/476 |
| 2014/0342844 | A1 | * | 11/2014 | Mooney ............. G06K 9/00342 473/266 |
| 2015/0038878 | A1 | * | 2/2015 | Pusch ................. A61B 5/1036 600/587 |

FOREIGN PATENT DOCUMENTS

| | | | |
|---|---|---|---|
| DE | 102006021788 A1 | 11/2007 | |
| DE | 102010003342 A1 | 9/2011 | |
| DE | 102012003033 A1 | 8/2013 | |
| DE | WO2013120573 A1 * | 8/2013 | ........... A61B 5/1036 |

* cited by examiner

METHOD FOR DETERMINING THE ALIGNMENT OF A SYSTEM, AND A DISPLAY SYSTEM

TECHNICAL FIELD

The invention relates to a method for determining the alignment or also for adjusting a system comprising measuring and display device, in which, using a measuring device, which has a measuring platform, horizontal and vertical forces as well as free moments, if applicable, are detected, which are exerted by a person located on the measuring platform, in which the person located on the measuring platform is photographed using at least one camera device, image data from the at least one camera device and measurement data from the measuring device are transmitted to the display device, and a force application line in the display device is superimposed on the image data and is displayed on the image of the person located on the measuring platform. The invention also relates to a display system for representing ground reaction forces, which are detected by a measuring platform on which a person stands, wherein the measuring platform has two measuring plates, which are decoupled from one another and which have sensors for detecting horizontal and/or vertical forces and/or free moments, comprising at least one camera device, which at least partially detects the person located on the measuring platform, and a display device, on which a force application line of the ground reaction forces are displayed superimposed on the person.

BACKGROUND

Display systems for representing ground reaction forces of a human being in response to the adjustment of a prosthetic or orthotic alignment is known from DE 10 2006 021 788 A1, for example. The vertical and horizontal components of a ground reaction force are detected via the sensor device and the force vector of the ground reaction force is projected onto the human body. This projection can be filmed.

U.S. Pat. No. 4,598,717 describes a display system for representing horizontal and vertical forces, which were captured via sensor units. The representation occurs on a monitor, on which the orientation, the location as well as the amount of the ground vector force are displayed. The image of the object to be examined is taken via a plurality of camera devices, the determined force vectors are superimposed on the camera image and are displayed. The display system is intended to display postural deformities as well as loads on different joint systems during a movement.

The representation of force application lines on the body itself is difficult, the filming of the person is cumbersome, and the storing and processing as well as the analysis of the data, in particular the quantification of the measurement data, is difficult or impossible to represent. A level of inaccuracy is furthermore present in the representation and an exact alignment and fixed geometric allocation of the projection device to the person is necessary.

SUMMARY

It is the object of the invention at hand to provide a method and a display system, by means of which in particular the setup of orthopedic devices, such as orthoses or prostheses can be measured, displayed and oriented, so that the forces introduced into the measuring platform can be represented correctly on an image as force application lines.

According to the invention, the object is solved by means of a method comprising the features of the main claim as well as a device comprising the features of the independent claim. Advantageous embodiments of the invention are disclosed in the subclaims, the description as well as the figures.

The method according to the invention for determining the alignment of a system comprising measuring and display device in which, using the measuring device, which has a measuring platform, horizontal and vertical forces and/or free moments are detected, which are exerted by a person located on the measuring platform, provides for the person located on the measuring platform to be at least partially photographed using at least one camera device, image data from the at least one camera device and measurement data from the measuring device to be transmitted to the display device, and the force application line in the display device to be superimposed on the image data and to be displayed on the image of the person located on the measuring platform, wherein marker points with a fixed geometric relation to the measuring platform are detected on the measuring platform by the at least one camera device, wherein the geometric relation of the marker points to one another, in particular the distance thereof to one another, is known, and the position and/or orientation of the measuring platform to the at least one camera device is determined via an image analysis of the detected marker points. It is thus possible to adjust the measuring and display system in such a manner that the force application line can be represented in a positionally accurate manner on the image of the person of the display device, whereby an improved adjustment, e.g. of a prosthetic alignment, can take place. By determining the alignment and adjustment, if applicable, it is no longer necessary to carry out a rigid geometric allocation of camera device and measuring platform; it is possible, in fact, to provide for a flexible setup and a simple transport of the system via a camera, which can be set up freely. Due to the fact that a projector does not need to be allocated to the measuring platform any longer, the system requires significantly lower production costs. The image data as well as the measurement data of the measuring platform can be supplied to an integrated documentation, which can be analyzed and used simultaneously during the measurement as well as subsequently, for example in connection with a follow-up meeting.

A mobile embodiment of the display device and an overall wireless transfer of all data makes it possible to involve the patient in the measurement, so that the patient can recognize immediately, which the impacts of a change to a setup or an alignment of orthoses or prostheses components to one another are on the force path, based on the representation of the force application line. A subsequent analysis can be carried out by means of the storage possibility of the image and measurement data, which are present in digital form, so that repeat measurements can be avoided. Perception errors on the patient are furthermore avoided and an independence of the representation from the prevailing light conditions is reached. By detecting the marker points, which are arranged on the measuring plate or which are at least in a fixed and known geometric allocation to the measuring plate, by means of the camera device, it is possible to determine the orientation, in particular the distance of the measuring plate to the camera device via the image analysis in the case of a certain and known distance of the marker points to one another, so that it is possible to calculate the exact distance as well as the exact orientation of the camera device to the force measuring plate and thus also the exact allocation of the measured force application lines to the respective position of the force measuring plate and thus the correct position of the force application line in the image. It is thus possible to display the respective force application lines at the location of the force introduction into the force measuring plate, independent from light conditions, alignment directions or the like, so that a positionally accurate superimposition of the representation of the force application line with the image or partial image of the person located on the measuring platform is ensured. Positionally accurate means that the force application line on the image is positioned at that location, at which the ground reaction force acts on the person.

Distortion characteristics of the camera device are considered to determine the orientation and/or position of the camera device relative to the measuring platform. Each camera device has certain optical or electronic distortion characteristics, the so-called intrinsic camera parameters, which are determined by means of a camera calibration, and which are invariant in terms of time. If these intrinsic camera parameters are known, they can also be considered in the calculation of the position of the respective force application lines relative to the image, whereby the accuracy of the representation of the force application line, the adjustment of the display and the determination of the alignment of the components of the system to one another is further increased.

The marker points can be embodied as glyphs, illuminants and/or reflector devices, and are either activated or illuminated to determine the alignment or adjustment. The activation or illumination can take place in the visible as well as in the invisible light spectrum.

Periodic light signals can be transmitted by the illuminant or can be transmitted to the reflector devices, so as to verify, whether the allocation of the camera device to the measuring platform is still at hand and has not changed. Certain light patterns can be requested in order to carry out a calibration and readjustment of the system. Advantageously, the measuring platform is oriented as horizontally as possible, which can be verified easily by means of a built-in level. In the case of an uneven ground, the horizontal orientated can be ensured via adjustable feet. The camera device is aligned as orthogonally as possible to the measuring platform, whereby, in the case of a plurality of camera devices, one is oriented frontally and one is oriented sagitally. On principle, it is also possible to detect via an image recognition, whether a frontal alignment or sagittal alignment is present. A plurality of camera devices can also be arranged on top of one another so as to be oriented in the same viewing direction, for example so as to be mounted to a support, whereby the accuracy of the adjustment is increased.

Markers are advantageously attached to the measuring platform so as to standardize the alignment of the patient to the measuring platform and thus also to the camera device. Advantageously, the longitudinal extension of the feet is thereby either vertically or parallel to the viewing direction of the camera device.

The determination of the alignment and the adjustment, if applicable, can take place periodically and/or after shifts or accelerations of the measuring platform or of the camera device have been determined. To reduce the calculating effort, it can be verified prior to a periodic determination of the alignment and/or adjustment, whether the measuring device was moved, for example, which can be determined by means of acceleration sensors in the measuring platform.

To further optimize the alignment of the system and the adjustment, if applicable, the measuring platform can be detected via an object recognition in a first image section and the image section of the camera device can be aligned automatically on a marking of the measuring platform or on a side edge of the measuring platform, so that the lower edge of the captured image section is flush with the front edge of the measuring platform facing the camera device, which is preferably embodied so as to be rectangular.

The image section can also be set automatically on the basis of an object recognition of the persons located on the measuring platform. On principle, the overall representation of the patient is of no interest, but only that of the lower extremities, so that a corresponding sectional setting can take place automatically, so as to concentrate the representation to what is significant.

A lighting device, from which an alignment beam is projected onto the measuring platform, can be allocated to the camera device, whereby the measuring platform can be aligned more easily to the camera device. The alignment can either be made manually by means of markings located on the measuring platform, in the alternative at least one light detector is arranged on the measuring platform to detect the alignment beam and to trigger a confirmation signal, when the camera device is aligned correctly and as optimally as possible to the measuring platform. Two or more light detectors can also be arranged downstream from one another, which are positioned in such a manner that a confirmation signal is output in response to a detection of the aligned beam by all light detectors. The light detectors can also serve as marking. When taking a photograph in the frontal plane, it is advantageous when the light detectors or sensors are arranged downstream from one another in the direction of the beam in the center of the measuring platform, thus along a center line or between two measuring plates, so that it is ensured that the measuring platform is oriented substantially parallel or vertically to the alignment light beam, and is thus also substantially aligned vertically or parallel to the viewing direction of the camera device.

The measurement data and the image data are preferably transmitted wirelessly to the display device. For this purpose, the components advantageously have transmitting devices and receiving devices, if applicable, so that the data can be transmitted and received via networks or the like. Typically, the display device is a portable display device, in particular a tablet, computer or smart phone, by means of which a highly accurate display on the one hand and a storing of the measurement data and of the image data on the other hand can be carried out. The tablet and the like can be used by the technician during the measuring or by the patient as mobile display unit. It is furthermore possible to show different setting aids in the live image, for example the distance of the force application lines to reference lines, or markers, which are attached to the prosthesis or the person.

The measurement data and the image data are preferably detected synchronously and with time identifier and are synchronized or output or stored with the same identifier, so that it is also possible on principle that the camera image is displayed superimposed directly with force application lines. Having the same identification means that the image data and measurement data with the same time identifier are superimposed on one another, so as to obtain a realistic reproduction of the force application line on the image or when playing the picture during measurement. On principle, it is also possible that a static picture and a subsequent analysis and superimposition are carried out. The image data and the measured values are stored with a corresponding time signal and are analyzed subsequently, this may be beneficial in the case of limited online calculating power. The display device can be placed on a tripod or a support either for the camera or a separate support. The tablet or another display device can further be connected to a projector or can be connected to another display, so that the content of the display device can also be made accessible to third parties.

If a plurality of camera devices are directed to the measuring platform from different viewing angles, a determination of the alignment and adjustment of the system and of the display of the force application line is made from the respective viewing angle, so that the representation can take place simultaneously on one or a plurality of display devices or representations of different views. If the image data and the adjustment or calibration data, respectively, of a plurality of camera devices are transmitted to the display device, a switch-over of the respective view can be made there, so that the technician or patient gains multidimensional insight into the force path.

To improve the adjustment, it is possible that glyphs, which are detected and are used for the image analysis, are arranged around the marker points. The marker points themselves can also be embodied as glyphs.

Optical markers or glyphs can be attached to the person and/or measuring platform, wherein the force application line and/or reference lines are aligned along the optical markers or glyphs or will be aligned. The markers as well as the glyphs can be active or passive, they can thus emit light either autonomously, even in the non-visible spectrum, or can reflect light beams emitted by a lighting element. On principle, it is also possible that an illuminant is attached to the tablet or another display device, so as to illuminate the reflectors with light accordingly.

In order to save calculating power for object recognition, an image can initially be captured with a large image section, wherein the measuring platform is detected via the object recognition and an image recognition is subsequently carried out in the areas of the marker points with a higher or larger resolution. Due to the more accurate examination of the marker points, which are in particular arranged on the corners of the measuring platform, the accuracy of the position detection of the markers and thus also of the orientation and positioning of the camera device relative to the measuring platform can take place in an improved manner.

Typically, the setup and the orientation of prosthetic components to one another are carried out at a uniform load of both lower extremities. Advantageously, the measuring platform is divided into two parts and is decoupled from one another at least in terms of force, so that the left leg and the right leg is positioned alternately on the respective force measuring plate. If a significant deviation of the weight distribution from the right plate to the left plate is determined, a warning signal can be output in order to avoid that an incorrect setup is set in response to an uneven loading.

All of the determined data of the measuring platform can be displayed on the tablet or the display device, thus the force application line, the force, the distribution of the forces, free moments as well as the change of the forces.

In addition to the displaying of images and measurement data with the same time identifier or of image and measurement data captured at the same time, a corresponding storing of all of the available perspectives and measurement data is provided.

Different output formats can likewise be provided, for example as image data, as measurement data, or as a PDF data.

The display system for representing ground reaction forces, which are detected by a measuring platform, on which a person stands, wherein the measuring platform has two measuring plates decoupled from one another, which have sensors for determining horizontal and/or vertical forces and/or free moments, using at least one camera device, which at least partially detects the person located on the measuring platform, and a representation device, on which the force application line of the ground reaction forces and a display of the person are displayed in a superimposed manner, provides for the measuring platform to have marker points with a fixed geometric relation to one another and a processing unit, in which the geometric relations, in particular distances from one other, are stored advantageously, wherein the processing unit is connected to the measuring platform, the camera device and the display device, or is integrated into one of the devices. As mentioned above, an automatic calculation of the allocation can take place via trigonometric calculations by including extrinsic parameters and intrinsic parameters of the camera via the marker points. When the camera is attached, for example, to a tripod at a certain height, the distance and the orientation of the camera device can be detected relative to the measuring platform via the angular orientation and the extrinsic, known data of the measuring platform and of the marker positions to one another.

The marker points can be embodied as illuminant, glyphs and/or reflectors, in particular the marker points can be embodied as LED, which can be switched on and off, in the visible spectral range or in the spectral range, which is not visible for the human being.

In addition to the horizontal and vertical force sensors, which are arranged in a sufficient number and orientation in or on the respective measuring plate so as to detect the necessary horizontal and vertical force components and free moments, the measuring platform can have an acceleration sensor, which detects impacts or movements of the measuring platform. If the measuring platform is moved by entering or by an impact, a readjustment and new calculation of the relative position of the respective force application lines in the image is performed automatically. Such an acceleration sensor can additionally or alternatively be allocated to the camera device.

A plurality of camera devices in different viewing angles can be directed to the measuring platform, so as to enable a simple switch-over and a more accurate representation of the force application lines on the captured image.

The camera device can be arranged on a support, from which a projector sends an alignment beam in the direction of the measuring platform. If at least one light detector is arranged on the measuring platform to detect the alignment beam, a confirmation signal can be output, if the orientation light beam hits the light detector or the light detectors. If no light detectors are provided, a desired orientation can be achieved easily via the alignment beam by aligning markers on the measuring platform.

An alignment device can be arranged, in particular so as to be extendable or compressible, in the measuring platform or on the measuring platform, for example in the form of a plastic strip, which has markings, onto which the support of the camera device is to be placed. This facilitates the desired alignment without requiring a rigid geometric allocation of camera device and measuring platform. In particular, the vertical alignment of the front edge of the measuring platform to the viewing direction of the camera and of the alignment beam, if necessary, is ensured in this manner.

BRIEF DESCRIPTION OF THE DRAWINGS

An exemplary embodiment of the invention will be explained in more detail below by means of the enclosed figures.

DETAILED DESCRIPTION

Figure 1:
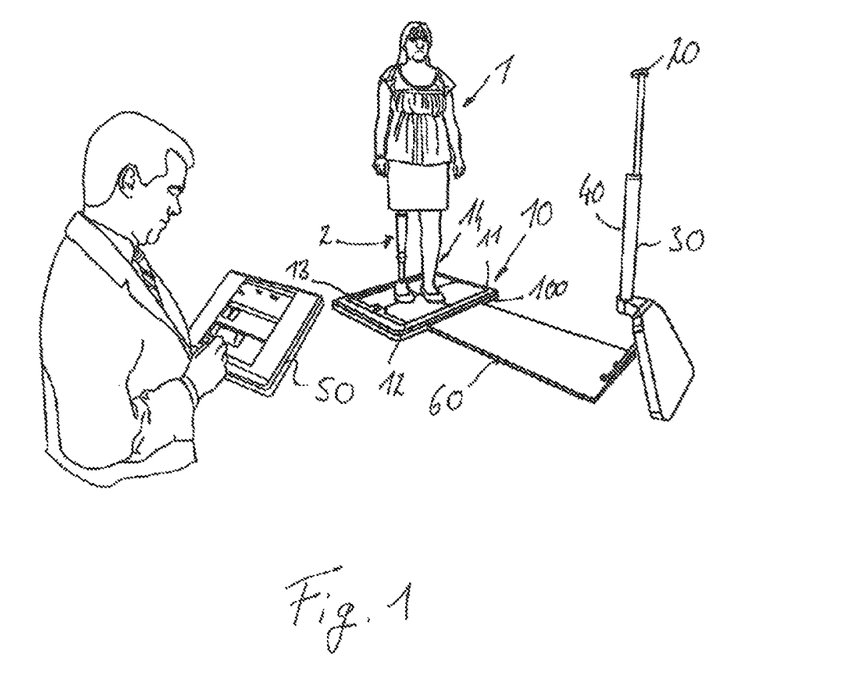
FIG. 1 shows an overall view of the system.

FIG. 1 shows a perspective representation of a system comprising a measuring device in the form of a measuring platform 10 and a camera device 20, which is mounted on a support 30. In the support 30, which can be adjusted in length to set the height of the camera device 20, a lighting device 40 is arranged to send an alignment light beam in the direction of the measuring platform 10. Advantageously, the orientation of the alignment light beam is identical with the central viewing direction of the camera device 20. The lighting device 40 can be embodied as laser beam, for example.

The measuring platform 10 is arranged in viewing direction of the camera device 20 frontally thereto, so that the leading edge 100 of the substantially rectangular measuring platform 10 is oriented vertically to the viewing direction of the camera device 20. To facilitate the alignment from the camera device 20 to the measuring platform 10, an alignment device 60 is provided on or in the measuring platform 10 in the form of an extendable mat, on or in the end of which, which faces the camera device 20, recesses or markings are arranged, which are placed into or on the feet of the support 30, so that an approximately vertical orientation of the leading edge 100 to the camera device 20 is ensured on the one hand and so that the distance between the camera device 20 and the measuring platform 10 is defined in a first approximation on the other hand. The alignment device 60 can also have a scaling, via which either the distance of the camera device 20 to the leading edge 100 of the measuring platform 10 can be read and can be input into a processing unit, so as to achieve an improved adjustment of the image of the camera device. The scaling can also be detected by the camera device 20 by means of an image recognition and can be transmitted automatically to a processing unit, so as to at least prepare the adjustment on the basis of the detected distance. On principle, however, the camera device 20 comprising the support 30 and the lighting device 40 are structurally decoupled from the measuring platform 10, so that freely selectable distances between the camera device 20 and the measuring platform 10 can be provided; the respective image section of the camera device 20 and the recognizability, which may be limited through this, of measuring platform 10 and of the person 1 located on the measuring platform 10 or the resolution and detectability, respectively, of marker points 11, 12, 13, 14 located on the measuring platform 10 serves as limitation.

It is advantageous, when the measuring platform 10 and the support 30 of the camera device 20 are on an equal level and the measuring platform 10 is aligned substantially horizontally. The height of the camera device 20 above the ground can be varied by means of the adjustable support 30. On the one hand, this serves to compensate for height differences of the ground and, on the other hand, to set the image section, depending on the size of the person 1 and on the orthopedic device 2 to be examined, such as orthosis or prosthesis.

FIG. 1 also shows a display device 50 in the form of a tablet, in which a processing device can also be integrated simultaneously to perform the adjustment of the measuring and display system. As an alternative to a calculation in the display device 50, it is possible that the measurement data of the measuring platform 10 as well as the image data of the camera device 20 are transmitted to a separate processing device, from which the processed data with the captured image of the person 1 and superimposed force paths of the ground reaction forces are also transmitted wirelessly to the display device 50, so that a calculation itself does not need to take place there, but only the display and possibly the storing and further processing is carried out.

On the upper side, four marker points 11, 12, 13, 14, which can either be embodied as reflectors or as self-luminous devices, such as LED or the like, are arranged on the measuring platform 10, which has two measuring plates 15, 16, which are decoupled from one another with regard to force and moment. The positions of the marker points 11, 12, 13, 14 to one another, thus also the distances of the marker points 11, 12, 13, 14 to one another, are known and are time-invariable, because the marker points 11, 12, 13, 14 are firmly mounted to the measuring platform 10. To be able to correctly display or show the contact points of the ground reaction forces and the size as well as orientation of the ground reaction forces on an image in the display device 50, the position on the image file must be set or adjusted correctly. On principle, the force application line 70 is an image superimposed on the image of the person 1 or the prosthesis 2, as it is illustrated in FIG. 1, the positioning of which must be carried out correctly on the image of the measuring platform 10. To be able to calculate this position accurately, the person 1 and the measuring platform 10 is initially detected via the camera device 20. The measuring platform 10 is identified via a common object recognition and marker points 11, 12, 13, 14 located thereon are determined. If the marker points 11, 12, 13, 14 are active lighting elements, which can operate in the visible as well as in the invisible spectrum, the processing unit or the tablet 50 can send a signal to the marker points 11, 12, 13, 14, when the adjusting process is to begin. In the embodiment of the marker points 11, 12, 13, 14 as reflectors, light signals, for example from the lighting device 40, are sent in the direction of the reflectors. In addition to the known distances between the marker points 11, 12, 13, 14, the camera characteristics with respect to the distortion characteristics are stored in the processing unit in the form of intrinsic camera parameters. The determination of the force application line position on the image data occurs by the calculation of the relations between the detected marker points 11, 12, 13, 14, the known geometric dimensions of the measuring platform 10 or the geometric relations between the marker points 11, 12, 13, 14, respectively, and the intrinsic parameters of the camera device 20.

Due to the fact that a rigid geometric allocation of the camera device 20 to the measuring platform 10 is not present, a regular inspection of the position of the marker points 11, 12, 13, 14 is made, so as to determine a possible shift of the measuring platform 10 to the camera device 20.

In addition to a purely optical analysis, it is possible that at least one acceleration sensor is arranged inside the measuring platform 10, via which a movement of the measuring platform 10 can be detected and a recalibration or readjustment can be triggered, if necessary. In the alternative or in addition, an acceleration sensor can also be allocated to the camera device 20.

Figure 2:
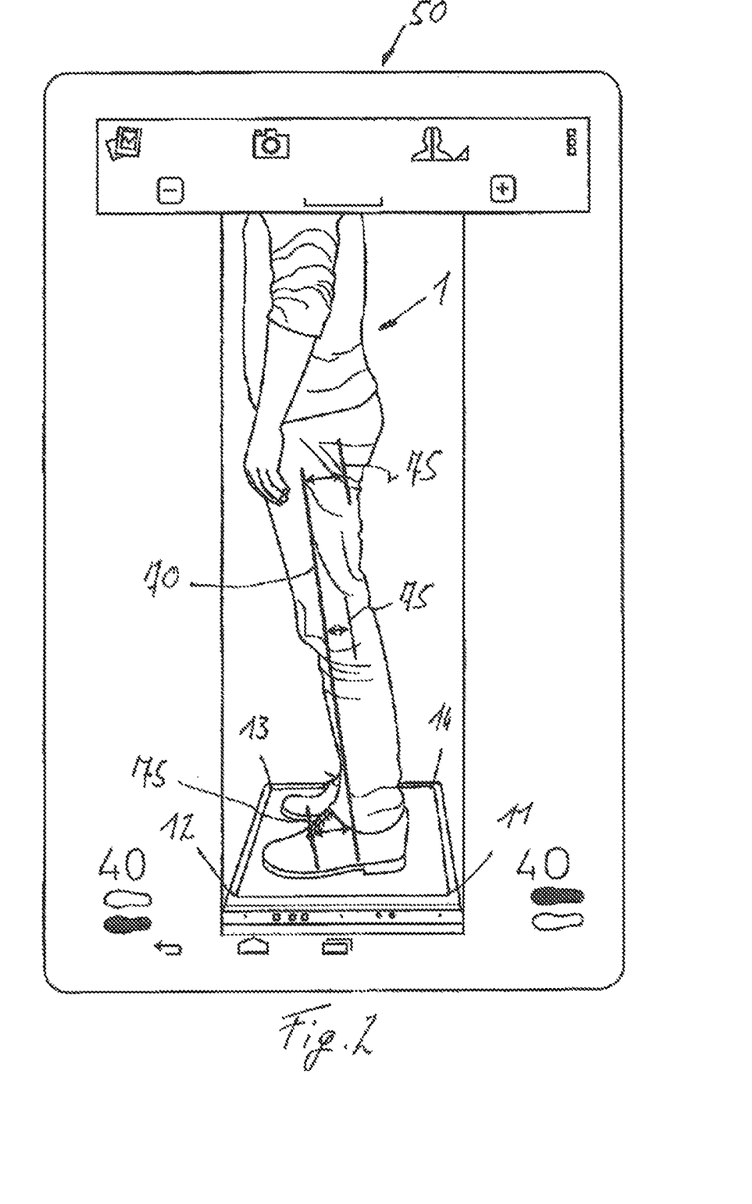
FIG. 2 shows a representation of the display device with shown force application line.

FIG. 2 shows the display device 50 in the form of a tablet. On principle, other display devices, such as laptops, computers, smart phones or the like, are suitable as well. The image of the person 1 standing on the measuring platform 10 can be seen on the display device 50. After detection of the marker points 11, 12, 13, 14, the image section was chosen in such a manner that the lower edge of the measuring platform 10 is flush with the lower image section. The relevant body area of the person 1 was also detected via the image recognition, and a corresponding lateral and height-related limitation of the image section was made automatically. The recognition of the marker points 11, 12, 13, 14 can be improved, if the measuring platform 10 and the marker points 11, 12, 13, 14 as a whole are detected initially and are reviewed subsequently with a higher accuracy or resolution of the areas of the marker points 11, 12, 13, 14. This can be supported by glyphs, which are arranged around the marker points 11, 12, 13, 14. Due to the above-described relations between the marker points 11, 12, 13, 14 and the image analysis of the images captured by means of the camera device 20, ground reaction forces captured separately for the left and the right leg by means of the measuring platforms 15, 16, can be shown correctly in the image. The force application line 70 is superimposed on the image of the person 1, wherein the force application point on the measuring platform 10 or the measuring plate 16 as well as the orientation of the ground reaction force is displayed.

The weight distribution on both force measuring plates 15, 16 is illustrated laterally next to the image section, the right as well as the left foot is in each case loaded equally with 40 kg in the illustrated exemplary embodiment. If an excessive difference is present between the two weight displays, a warning signal, which prompts to correct the posture of the person, so that a technician can set the non-illustrated prosthesis 50 correctly, can be output via the display device 50 or via a separate warning device.

Distances to reference points or reference lines 75 are also represented in FIG. 2, so as to make it easier for the technician to set a prosthetic alignment. The distance of the force application line 70 to a previously determined reference position, which is determined as a function of the total foot length, is displayed in the area of the foot. In the knee area, the reference line is the distance of the ground reaction force from the pivot point of the knee, in the hip area it is distance to the pivot point of the hip.

The measurement data of the measuring platform 10 as well as the images can be stored in a synchronized manner in the display device 50, and all existing perspectives and measurement data can be stored in a synchronized manner in the case of a plurality of camera devices 20, so that a subsequent analysis of the measuring results and of the image data can be carried out easily. All of the data transport paths are preferably wireless, so as to allow unrestricted mobility. The reference lines 75 or reference points can be shown and changed in the image. In addition to the representation of the measuring results and of the captured image data with the same time identifier, they can also be output and printed out, if applicable, as still images. The respective perspective of the camera device 20 can be carried out automatically by an object recognition of the captured image data.

In addition to the use of a plurality of camera devices from different viewing angles, for example frontally and sagitally, it is also possible to arrange two camera devices on top of one another, resulting in an improved accuracy in the image analysis and the allocation of the ground reaction forces to the image data.

Advantageously, the measuring platform 20 is oriented as vertically as possible to the viewing direction of the respective camera device 20, but deviations are possible. To facilitate the allocation, the feet of the person 1 are placed inside markings on the measuring platform or are aligned to them.

Figure 3:
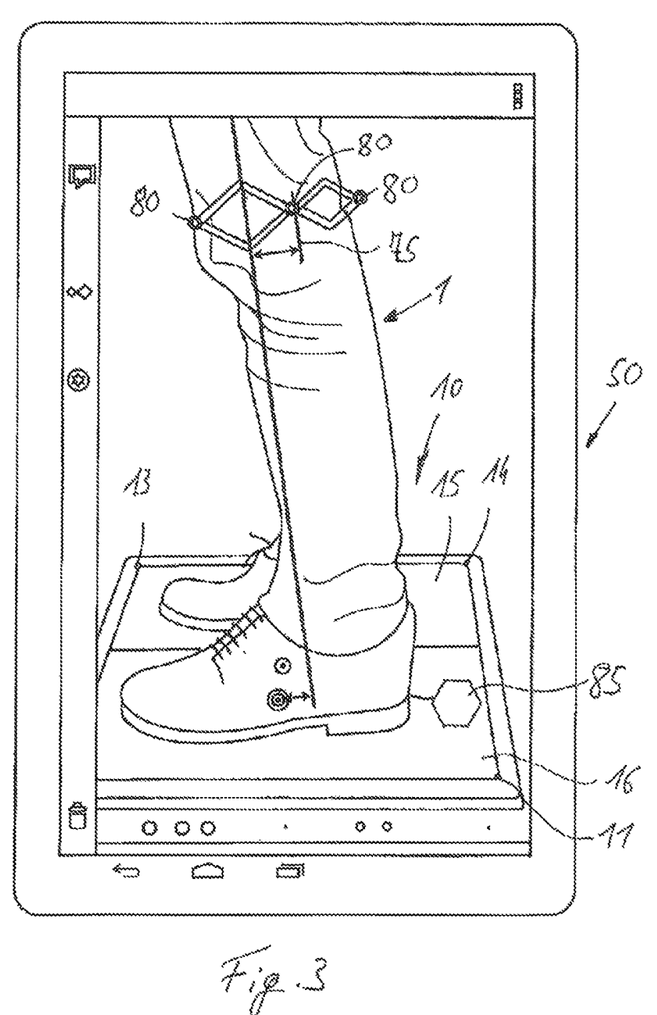
FIG. 3 shows a representation with subsequent analysis and documentation.

FIG. 3 shows an illustration of a measuring view for subsequent analysis and documentation, in which markers 80 are arranged on the person 1. A facilitated allocation of significant points on a prosthetic foot, a lower leg tube or on a prosthetic knee joint can be made via the markers 80, which can also be embodied as glyphs. This makes it easier to detect the desired distance of the force application line 70 to the respective significant points and to adjust the prosthetic or orthotic device until the desired distances, which are marked or shown, are reached. The distances can be calculated automatically via an image capturing, because a quantitative statement about the position of the force application line 70 to the respective marker points 80 can also be made due to the known relations between the marker points 11, 12, 13, 14. The insertion of notes in a comment field 85 is also possible due to the storage of the image data.

Figure 4:
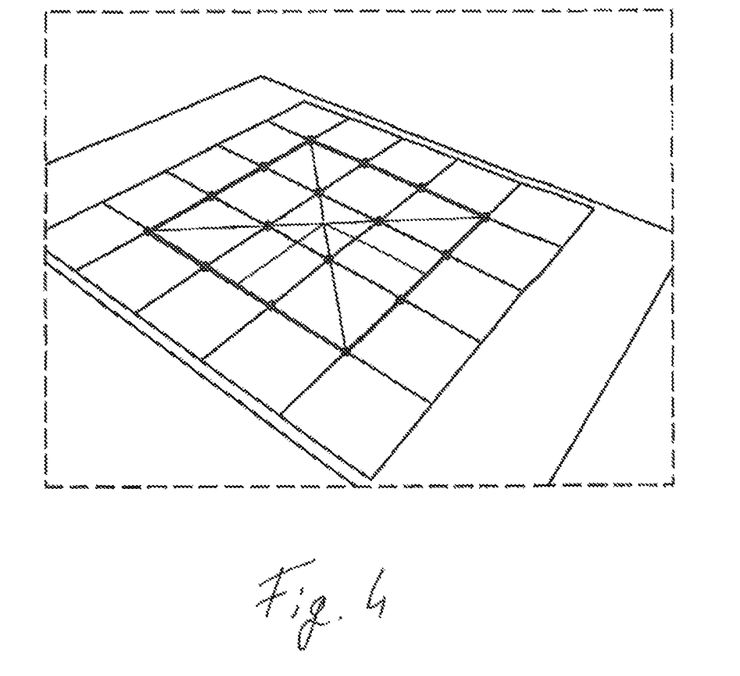
FIG. 4 shows a schematic representation for determining a relative spatial position of an object.

FIG. 4 shows a schematic representation of a force measuring plate with checkered pattern, for explaining the calculation of the respective relevant position of the starting point of the non-illustrated force application line 70. Via the known corner points, which represent the corner points of the enclosed chessboard in FIG. 4, it is possible to calculate the spatial position of an object located thereon, for example of the person, and of a fictitious object, for example the force application line 70. In addition to the intrinsic camera parameters, the actual distances between the outer corner points of the checkerboard pattern to one another are known, so that the respective position is calculated on the basis of trigonometric calculations.

Figure 5:
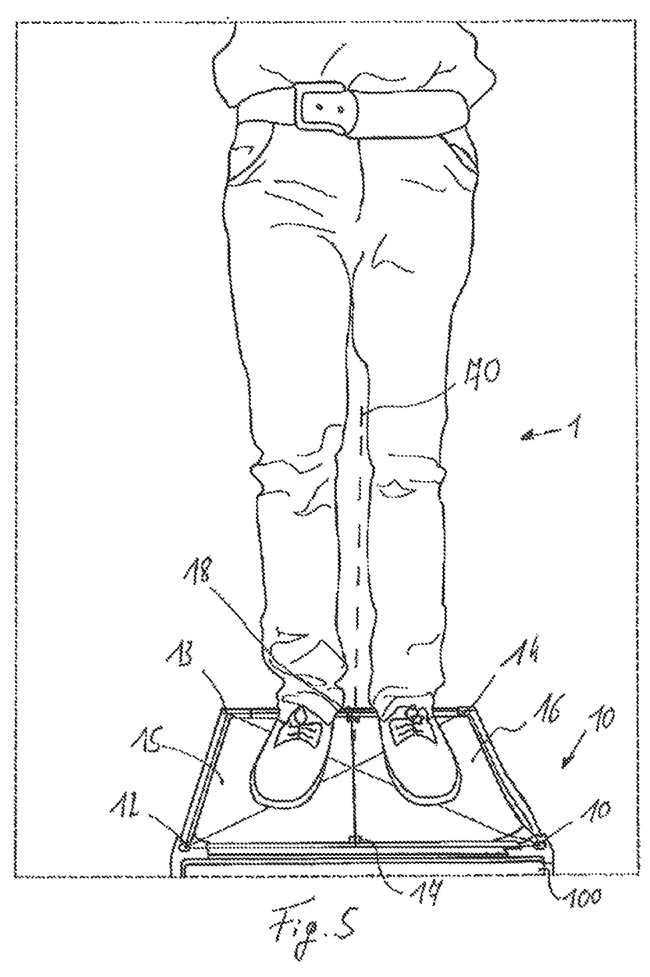
FIG. 5 shows a representation of the result of the adjustment process.

FIG. 5 shows the result of an adjustment process, in which the leading edge 100 of the measuring platform 10 is flush with the lower image section. The four marker points 11, 12, 13, 14 are arranged in the corners of the measuring platform, the measuring platform has two effective measuring plates 15, 16, which are independent from one other, via which vertical and horizontal forces are determined. Two light detectors 17, 18, which serve to align the measuring platform 10, are furthermore arranged in the center between the two force measuring plates 15, 16. If an alignment light beam is thrown in the direction of the measuring platform 10 and runs through both light detectors 17, 18, the measuring platform 10 is aligned vertically thereto and a confirmation signal can sound or can be output. If the alignment light beam does not run through both light detectors 17, 18, a correction must be made.

The force application line 70, here only the center of gravity line, is superimposed on the image of the person 1, the respective coordinates are allocated to the force application point of the force path 70 via the image recognition.

The invention claimed is:

1. A method for determining an alignment of a system, the method comprising:

providing the system with a measuring device, a display device, and at least one camera device, the measuring device having a measuring platform;

detecting with the measuring device horizontal and vertical forces that are exerted by a person located on the measuring platform;

photographing at least a portion of the person located on the measuring platform using the at least one camera device;

transmitting image data from the at least one camera device and measurement data from the measuring device to the display device, the image data representing an image of the at least a portion of the person;

superimposing a force application line in the display device on the image data;

displaying the force application line on the image;

detecting marker points with a fixed geometric relation to the measuring platform with the at least one camera device, wherein the geometric relation of the marker points to one another is known;

determining at least one of a position and an orientation of the measuring platform relative to the at least one camera device via an image analysis of the detected marker points;

adjusting the system at a reoccurring time interval, or adjusting the system in response to detecting, with at least one sensor, shifts or accelerations of at least one of the measuring platform and the at least one camera device, wherein the adjusting the system includes adjusting the displayed force application line or determining at least one of the position and the orientation of the measuring platform relative to the at least one camera device.

2. The method according to claim 1, wherein distortion characteristics of the at least one camera device are considered to determine at least one of the orientation and the position of the camera device relative to the measuring platform.

3. The method according to claim 1, wherein the marker points comprise at least one of glyphs, illuminants, and reflector devices, the marker points being activated or illuminated to determine the alignment of the system or the adjusting the system.

4. The method according to claim 3, wherein the illuminants emit light in a non-visible spectrum.

5. The method according to claim 1, wherein the measuring platform is detected via an object recognition, and an image section of the at least one camera device is aligned automatically on a marking of the measuring platform or on a side edge of the measuring platform.

6. The method according to claim 5, wherein the image section is set automatically on a basis of the object recognition of the person located on the measuring platform.

7. The method according to claim 5, wherein the image is initially captured with a first image section, the measuring platform is detected via the object recognition, and the object recognition is subsequently carried out in areas of the marker points with a first resolution.

8. The method according to claim 1, wherein a lighting device is allocated to the at least one camera device, the lighting device projecting an alignment beam onto the measuring platform, the measuring platform being aligned to the alignment beam.

9. The method according to claim 1, wherein the at least one camera device includes a plurality of camera devices that are directed to the measuring platform from different viewing angles and an alignment is made from one or more of the viewing angles.

10. The method according to claim 1, wherein glyphs, which are arranged around the marker points, are detected and are used for the image analysis, or the marker points are embodied as glyphs.

11. The method according to claim 1, wherein a warning signal is output when an uneven loading of the measuring platform is determined.

12. The method according to claim 1, wherein the force application line is displayed in a positionally accurate manner on the image.

13. The method according to claim 1, wherein the measurement data and the image data are transmitted wirelessly to the display device.

14. The method according to claim 1, wherein the measurement data and the image data are detected with a time identifier and are output or stored in a synchronized manner.

15. The method according to claim 1, wherein free moments are displayed.

16. The method according to claim 1, wherein the geometric relation of the marker points to one another is stored in a processing unit of the system.

* * * * *